United States Patent [19]

Barcus et al.

[11] Patent Number: 5,160,789
[45] Date of Patent: Nov. 3, 1992

[54] FIBERS AND PULPS FOR PAPERMAKING BASED ON CHEMICAL COMBINATION OF POLY(ACRYLATE-CO-ITACONATE), POLYOL AND CELLULOSIC FIBER

[75] Inventors: Robert L. Barcus, Springfield Twp.; David W. Bjorkquist, Wyoming, both of Ohio

[73] Assignee: The Procter & Gamble Co., Cincinnati, Ohio

[21] Appl. No.: 458,265

[22] Filed: Dec. 28, 1989

[51] Int. Cl.$^5$ ............................................. D02G 3/00
[52] U.S. Cl. ..................................... 428/361; 8/115.51; 8/115.6; 8/116.1; 162/157.1; 162/157.6; 162/146; 428/359; 428/364; 428/375; 428/392; 428/393; 527/303; 527/314
[58] Field of Search ............... 428/359, 361, 364, 375, 428/393, 392; 8/115.51, 115.6, 116.1; 162/157.1, 157.6, 146; 527/303, 314

[56] References Cited

U.S. PATENT DOCUMENTS

| | | | |
|---|---|---|---|
| 3,301,746 | 1/1967 | Sanford et al. | 162/113 |
| 3,366,582 | 1/1968 | Adams et al. | 260/2.5 |
| 3,589,364 | 6/1971 | Dean | 128/284 |
| 3,678,031 | 7/1972 | Schoggen | 260/231 |
| 3,759,861 | 9/1973 | Shimokawa | 260/31.4 |
| 3,858,585 | 1/1975 | Chatterjee | 128/290 |
| 3,889,678 | 6/1975 | Chatterjee et al. | 128/284 |
| 3,905,863 | 9/1975 | Ayers | 162/113 |
| 3,954,721 | 5/1976 | Gross | 526/14 |
| 3,974,025 | 8/1976 | Ayers | 162/113 |
| 3,989,586 | 11/1976 | Bashaw et al. | 162/168 |
| 3,994,771 | 11/1976 | Morgan, Jr. et al. | 162/113 |
| 4,018,951 | 4/1977 | Gross | 427/401 |
| 4,128,692 | 12/1978 | Reid | 428/378 |
| 4,151,130 | 4/1979 | Adams | 260/17.4 |
| 4,165,743 | 8/1979 | Denning | 128/290 |
| 4,191,609 | 3/1980 | Trokhan | 162/113 |
| 4,210,489 | 7/1980 | Markofsky | 162/164 |
| 4,252,761 | 2/1981 | Schoggen et al. | 264/120 |
| 4,295,987 | 10/1981 | Parks | 252/194 |
| 4,300,981 | 11/1981 | Carstens | 162/109 |

(List continued on next page.)

FOREIGN PATENT DOCUMENTS

| | | |
|---|---|---|
| 1085810 | 9/1981 | Canada . |
| 192216 | 8/1986 | European Pat. Off. . |
| 50-5610 | 1/1975 | Japan . |
| 1540133 | 2/1979 | United Kingdom . |
| 1559716 | 1/1981 | United Kingdom . |

OTHER PUBLICATIONS

Gantrez AN Technical Data Sheet, GAF Corp.
Hebeish, Springer-Verlag, 1981; "The Chemistry and Technology of Cellulosic Copolymers".
Re. 32,649 Reissue of Brandt et al., supra.
J. Macromolecular Science-Rev. Macromol. Chem. Phys. (26(1)), pp. 69-80 (1986).
Ward, K., Jr., "Chemical Modification of Papermaking Fabrics", (Mercel Dekker, Inc. NY: 1973) pp. 167-170.
Hirose, S and Hatakeyama, H "Graft Copolymerization of Vinyl Monomers on Cellulose Using Peroxyacetic Acid-Ferrous Ion Redox Initiator System," J. of Applied Polymer Science, vol. 37, pp. 1119-1129 (1982).
"Source-Based Nomenclature for Copolymers" IUPAC-Macromolecular Division: Commission on Macromolecular Nomenclature (IUPAC 1985).

Primary Examiner—Lorraine T. Kendell
Attorney, Agent, or Firm—Katherine Lynn Stewart; Rose Ann Dabek; Jerry J. Yetter

[57] ABSTRACT

Disclosed is a fiber comprising, chemically bonded together, (a) a conventional cellulosic fiber, such as a Kraft fiber or a chemithermomechanical pulp fiber; (b) poly(acrylate-co-itaconate), such as the acid form of a poly(acrylate-co-itaconate) comprising 90-95 mole % acrylate and 5-10 mole % itaconate having weight and (c) a polyol, such as polyethylene glycol; also disclosed are methods for making such fibers, especially evaporatively depositing an intimate mixture of the copolymer and polyol on the fiber followed by thermally crosslinking at specific temperatures for limited periods; absorbent paper which can be made by wet-laying the fiber, especially in admixture with conventional fiber; and derivative paper structures, such as multi-ply disposable absorbent towels.

14 Claims, 1 Drawing Sheet

U.S. PATENT DOCUMENTS

| | | | |
|---|---|---|---|
| 4,354,901 | 10/1982 | Kopolow | 162/158 |
| 4,391,878 | 7/1983 | Drach | 428/479 |
| 4,440,597 | 4/1984 | Wells et al. | 162/111 |
| 4,469,735 | 9/1984 | Trokhan | 428/154 |
| 4,552,618 | 11/1985 | Kopolow | 162/157.1 |
| 4,610,678 | 9/1986 | Weisman et al. | 604/368 |
| 4,637,859 | 1/1987 | Trokhan | 162/109 |
| 4,654,039 | 3/1987 | Brandt et al. | 604/368 |
| 4,721,647 | 1/1988 | Nakanishi et al. | 428/283 |
| 4,748,076 | 5/1988 | Saotome | 8/116.1 X |
| 4,780,500 | 10/1988 | Sinka et al. | 524/559 |
| 4,865,886 | 9/1989 | Itoh et al. | 8/116.1 X |
| 4,888,238 | 12/1989 | Katz et al. | 428/378 |

FIBERS AND PULPS FOR PAPERMAKING BASED ON CHEMICAL COMBINATION OF POLY(ACRYLATE-CO-ITACONATE), POLYOL AND CELLULOSIC FIBER

FIELD OF THE INVENTION

This invention relates to fibers, such as Kraft fibers, which are chemically modified with certain poly(arcylate-co-itaconate) copolymers and polyols; to chemical methods for making such fibers; to improved paper which can be made by wet-laying the fibers, especially as a pulp in admixture with conventional papermaking pulps; and to derivative paper structures, such as multiply disposable absorbent towels.

BACKGROUND OF THE INVENTION

The is an ongoing interest in the development of absorbent articles such as paper towels. Disposable paper towels are widely used in the home for wiping spills, especially of water or watery liquids; for cleaning work-surfaces such as those of the kitchen and bathroom; for food preparation and handling; or for cleaning glass. More generally, absorbent papers are sometimes incorporated into other absorbent articles, such as dressings, catamenials and disposable diapers.

Manufacturing, more specifically sheet-forming, processes for paper are well-established in commerce. Papermaking machinery is very capital-intensive, and as a result, improvements in absorbent paper which do not require any major change in, or complication of, the paper-forming process tend to be highly appreciated. The processes of major importance include air-laying and wet-laying.

In outline, the latter process involves filtering a dilute dispersion of fibers onto a mesh (usually termed a Fourdrinier wire) and drying the resulting web. There is a large installed base of manufacturing equipment using continuous, high-speed machinery based on the wet-laying technique, representing considerable investment.

Conventional papermaking fibers suitable for wet-laying papermaking are cellulosic fibers which disperse well and can readily be filtered and dried. They typically absorb relatively small amounts of water, of the order of a few grams per gram of bone dry fiber.

The simplest notion for improving the absorbency of paper involves adding thereto a highly water-absorbent material, such as one of the gel-forming polycarboxylate polymers, which are well-known in the art. Very high absorbencies are possible, of the order of hundreds of grams of water per gram of polymer. Such materials have found particular utility as disposable diaper "superabsorbents".

Superabsorbents are however inherently very difficult to handle in a wet-laying process. Thus they tend to disintegrate under the relatively high shear forces involved in wet-laying papermaking. Moreover, they are difficult to filter, tending to block the Fourdrinier wire; and once deposited, they are very difficult to dry. The final product tends to be stiff and may not rewet to an acceptable degree when in use.

Applying the above-identified simple absorbency-improving notion to processes other than wet-laying has led to the development of a laminated structure or "sandwich" having outer plies of conventional paper and an inner layer consisting essentially of superabsorbent. However, the superabsorbent tends to leak out from the product paper structure, especially through pinholes or when the paper structure is torn. Slippery, gel-like material is released, which is a serious aesthetic disadvantage.

The deficiencies of the above approaches suggest a need to consider more than just the absolute magnitude of the absorbency which can be had from a particular paper additive. Thus, although absorbency is of primary importance, other requirements, such as ease of manufacture and product aesthetics, must be met. In addition, as distinct from water-absorbing capacity, another problem which has been identified in the context of absorbent structures has to do with rate of water uptake, in technical terms, "wicking rate". Wicking rate is particularly important in a disposable paper towel which must quickly absorb a spill.

In principle, it is possible to suggest making absorbent paper by wet-laying an improved absorbent fiber (as distinct from particulate superabsorbents on one hand or conventional papermaking fibers on the other). However it would seem that these reports of "absorbent fibers". However it would seem that these often involve mere physical coating of a fiber, such as processes involving precipitating absorbent polymers onto fibers or polymerizing monomers such as acrylic acid and methylenebisacrylamide in the presence of a fiber. In such situations, the chemical means are not present to covalently attach the polymer to the fiber. In consequence, the coating may not survive the shear forces involved in typical wet-laying operations, and may come off, the result being wire-blocking and/or drying problems similar to those mentioned above.

Grafted fibers are also well-known. Typical of grafted fibers are those made by graft copolymerizing methyl acrylate and cellulosic fibers in the presence of an appropriate catalyst such as cerium (IV) ammonium nitrate followed by hydrolyzing to the absorbent form. Absorbent grafted fibers are often not as strong as might be desired for wet-laying papermaking, since the low molecular weight monomer used in the preparation is capable of penetrating the fiber, polymerizing in the interior, so that when hydrolyzed and exposed to water, the fiber "balloons" internally and can easily shatter.

Various highly absorbent polymers have been extruded, and the extrudates have sometimes been termed "fibers". However, these materials are in fact not fibers in the usual sense of cellulosic papermaking fibers, rather they tend to be chemically homogeneous, and as with the common particulate superabsorbents, form slippery gels and encounter processing problems when wet-laid.

Oddly, to add to the above, there are reports in the literature of various chemicals apparently similar to those used herein apparently imparting wet-strength and/or hydrophobicity, i.e., water-resistance, to paper.

In view of the foregoing considerations, improvements in absorbent cellulosic fibers which do not make the fiber incompatible with wet-laying are highly desirable.

Accordingly, it is an object of the instant invention to provide a wet-layable papermaking fiber and pulp having an improved absorbent form.

More specifically, it is an object herein to provide a chemically modified fiber (hereinafter "the fiber of the invention") having three chemically bonded components, namely a cellulose of natural origin (such as an ordinary pulp fiber), a poly(acrylate-co-itaconate) and a polyol; which fiber has a water-absorbent chemical form (such as the sodium salt form), which is useful especially in that it is readily capable of being distributed into a web by wet-laying (e.g., as a pulp) in admixture with untreated fibers.

It is another object of the invention to provide absorbent wet-laid paper comprising the fiber of the invention.

A further object of the invention is the provision of a suitable process, unreliant on metal catalysts as used in common grafting processes of the art, for reproducibly making the fiber of the invention.

These and other objects are secured, as will be seen from the following disclosure.

BACKGROUND ART

For general discussion of coatings and chemical modifications of papermaking fibers and of paper see "Pulp and Paper, Chemistry and Chemical Technology", Ed. James P. Casey, Wiley-interscience, 1981, Vols. I-IV. See also "Chemical Modification of Papermaking Fibers", K. Ward, Marcel Dekker, N.Y., 1973.

Japanese Laid-Open 50-5610, Jan. 21, 1975, discloses treating a preformed paper web with an aqueous solution containing polyvinylalcohol and various copolymers, especially maleic anhydride-methyl vinyl ether, followed by drying and thermally treating, to form high-wet-strength papers.

Papermaking wet-strength resins based on half-amides derived from maleic anhydride copolymers with various monomers are disclosed in U.S. Pat. No. 4,391,878, Drach, issued Jul. 5, 1983.

Papermaking sizing agents and adhesives based on carboxylated vinyl polymers are disclosed in U.S. Pat. No. 3,759,861, Shimokawa, issued Sep. 18, 1973.

Gantrez AN Technical Data Sheet, GAF Corp., suggests a number of useful applications for Gantrez polymers in connection with papermaking. Notably, Gantrez is suggested for use "as a beater additive to improve sizing, strength and dimensional stability." Further, "as a paper coating component, it can improve moisture . . . resistance."

U.S. Pat. No. 4,018,951, Gross, issued Apr. 19, 1977, discloses absorbent films prepared by heating methyl vinyl ether-maleate copolymers with crosslinking agents such as diglycidyl ethers or dihaloalkanes. The films can assertedly be used in absorbent articles.

U.S. Pat. No. 4,128,692, Reid, issued Dec. 5, 1977, discloses precipitating absorbent polymers onto fibers from an aqueous slurry.

U.S. Pat. No. 4,721,647, Nakanishi et al, issued Jan. 26, 1988, discloses an absorbent article comprising hydrophobic fibers and a water-absorbent polymer as spherical particles.

U.S. Pat. No. 4,295,987, Parks, issued Oct. 20, 1981, discloses a two-ply paper towel containing powdered absorbent copolymers. A layer can be sandwiched between two paper plies.

Brandt et al, U.S. Pat. No. 4,654,039, issued Mar. 31, 1987, reissued as RE 32,649 on Apr. 19, 1988, disclose superabsorbent polymers which can be used in absorbent structures.

Weisman, U.S. Pat. No. 4,610,678, issued Sep. 9, 1986, discloses air-laid absorbent structures comprising a mixture of hydrophilic fibers and discrete particles of a water-insoluble hydrogel.

Saotome, EP-A 192,216, published Aug. 27, 1986, discloses a water-absorbent fibrous structure, characterized as comprising a fibrous cellulosic material impregnated with a water-absorbent acrylic polymer and a fibrous material, which is produced by a method in which an aqueous solution of a monomeric component comprising acrylic acid and a radical initiator is diffused in a fibrous cellulosic material and heated, followed by blending with a fibrous material.

See also U.S. Pat. No. 4,354,901, Kopolow, issued Oct. 19, 1982 and U.S. Pat. No. 4,552,618, Kopolow, issued Nov. 12, 1985. The Kopolow disclosures relate to compression or heat treatment of boards in the dry state after a wet-laying papermaking process. The boards comprise "hydrocolloidal fibers" such as those of U.S. Pat. No. 3,889,678, Chatterjee et al, issued Jun. 17, 1975.

Heat treatment of absorbent carboxyalkyl cellulose fibers in an absorbent structure to derive improved fluid absorptive properties is disclosed in U.S. Pat. No. 3,858,585, Chatterjee, issued Jan. 7, 1975.

Grafted, hydrolyzed absorbents are disclosed in "The Chemistry and Technology of Cellulosic Copolymers", Hebeish, Springer-Verlag, 1981; see also U.S. Pat. No. 3,366,582, Adams et al, issued Jan. 30, 1968 and U.S. Pat. No. 4,151,130, Adams issued Apr. 24, 1979.

U.S. Pat. No. 4,151,761, Schoggen et al, issued Feb. 24, 1981, discloses sheets prepared from certain modified fibrous carboxymethylcellulose derivatives, sometimes known as bibulous cellulosic fibers. Such sheets are disclosed in patents including U.S. Pat. No. 3,678,031, Schoggen, issued Jul. 18, 1972 and U.S. Pat. No. 3,589,364, Dean and Ferguson, issued Jun. 29, 1971.

U.S. Pat. No. 4,780,500, Sinka et al, issued Oct. 25, 1988, discloses a coating composition for paper and paperboard containing pigment, binder, lubricant and water. The composition comprises a copolymer of 80%-98% (wt.) acrylic acid and 2%-20% (wt.) itaconic acid. The copolymer is water dispersible, has a molecular weight of 100,000-800,000 and is in acid, sodium, potassium and/or ammonium salt form. Included are compositions comprising by way of copolymer 95% (wt.) sodium acrylate and 5% (wt.) diammonium itaconate and having $M_W$ 250,000-400,000. Such copolymers can be used at a low level (0.05%-0.8% wt.) based on solids in the coating composition as a retention aid to retard release of water from the coating composition without increasing its viscosity.

Patents relating to papermaking processes generally useful in the context of the present invention and incorporated herein by reference include U.S. Pat. No. 3,301,746, Sanford et al, issued Jan. 31, 1967; U.S. Pat. No. 3,905,863, Ayers, issued Sep. 16, 1975; Morgan, Jr. et al, issued Nov. 30, 1976; U.S. Pat. No. 4,191,609, Trokhan, issued Mar. 4, 1980; U.S. Pat. No. 4,300,981, Carstens, issued Nov. 17, 1981; U.S. Pat. No. 4,440,597, Wells et al, issued Apr. 3, 1984; U.S. Pat. No. 4,469,735, Trokhan, issued Sep. 4, 1984; and U.S. Pat. No. 4,637,859, Trokhan, issued Jan. 20, 1987.

SUMMARY

The present invention relates to a chemically modified fiber which has good absorbent properties. The fiber comprises, chemically bonded together, (a) a cellulosic fiber, very preferably a Kraft or chemithermomechanical fiber; (b) a poly(acrylate-co-itaconate) preferably having a relatively high acrylate content and a relatively low itaconate content; and (c) a polyol, very preferably a polyethylene glycol.

In more detail, the invention encompasses a chemically modified fiber having a water absorbency and retention value in the range from about 15 g/g to about 130 g/g comprising, chemically bonded together: (a) a cellulosic fiber selected from the group consisting of chemithermomechanical pulp fiber, bleached hardwood Draft pulp fiber, bleached softwood Kraft pulp fiber, unbleached hardwood Kraft pulp fiber, unbleached softwood Kraft pulp fiber, bleached softwood sulfite pulp fiber, unbleached softwood sulfite pulp fiber, cotton linters, mercerized dissolving pulp fiber, unmercerized dissolving pulp fiber, and mixtures thereof; (b) a poly(acrylate-co-itaconate) having a weight average molecular weight in the range from about 60,000 to about 1,000,000, an acrylate content of from about 50 mole % to about 99 mole % and an itaconate content of from about 1 mole % to about 50 mole %, and (c) a polyol; wherein the proportion by weight of said poly(acrylate-co-itaconate) to polyol is from about 250:1 to about 3:1 and the weight of said poly(acryiate-co-itaconate) plus said polyol per unit weight of said cellulosic fiber, (a), is in the range from about 0.3 to about 2, the poly(acrylate-co-itaconate) weight being expressed on an acid equivalent basis.

In the above, a preferred polyol has formula $HO(CH_2CH_2O)_nH$ wherein n is from about 4 to about 154 and a preferred proportion by weight of poly(acrylate-co-itaconate) to polyol is from about 30:1 to about 4:1.

In a highly preferred embodiment, the invention provides a chemically modified fiber wherein said poly(acrylate-co-itaconate) has acrylate content of from about 90 mole % to about 95 mole % and itaconate content of from about 5 mole % to about 10 mole %; said weight average molecular weight is in the range from about 600,000 to about 900,000; n is said formula is from about 34 to about 100; and said weight of poly(acrylate-co-itaconate) plus polyol per unit weight of said cellulosic fiber, (a), is in the range from about 0.6 to about 1.5.

In other absorbent, quick-wicking chemically modified fiber embodiments, n in said formula is from about 70 to about 80; said proportion by weight of poly(acrylate-co-itaconate) to polyol is from about 10:1 to about 5:1; and said weight of poly(acrylate-co-itaconate) plus polyol per unit weight of cellulosic fiber, (a), is in the range from about 0.8 to about 1.2. Such fiber of the invention is especially useful when said water absorbency and retention value is in the range from about 50 g/g to about 90 g/g.

In the above-identified fiber of the invention, cations, which are inherently present in a charge-balancing amount, are generally selected from the group consisting of sodium, potassium, lithium, hydrogen and mixtures thereof, more preferably sodium, hydrogen and mixtures thereof.

A highly preferred form of the fiber for absorbency purposes is the sodium salt form, however the acid form is also useful, inter-alia because it can readily be taken to the absorbent form by sodium hydroxide.

The invention encompasses papermaking pulps especially useful for wet-laying (although the same pulps are also useful in air-laying applications). Cellulosic papermaking pulps in accordance with the invention consist essentially of the above-identified fiber, or can be a mixture of the fiber of the invention with an unmodified fiber, such as the unmodified component (a) fiber identified supra. One such pulp consists essentially of: from about 5% to about 60% of the chemically modified fiber of the invention and from about 40% to about 95% of conventional cellulosic fiber.

Preferred chemically modified pulps in accordance with the invention are useful in the acid form, for example the pulp is largely acid-form when the content of cations which are hydrogen is such as to produce a pH of less than 5 when the pulp is dispersed in water. In this instance, the consistency can vary widely and the pulp can be shipped at high consistency since, as noted above, the chemically modified fiber is not absorbent.

The invention also encompasses the absorbent form of the cellulosic papermaking pulp, for example one comprising a major proportion of sodium-form fiber of the invention: typically, in such a pulp, the content of cations which are hydrogen is such as to produce a pH of about 6 to about 9 when dispersed in water.

The fiber of the invention is a lightly crosslinked material. Particular attention is paid herein to adjusting the relative proportions of the starting-material components and to process conditions so that a lightly crosslinked fiber can best be achieved.

Thus a preferred fiber of the invention can be secured by heating for specific curing times at particular curing temperatures a conventional cellulosic fiber onto which has been deposited an intimate mixture of the poly(acrylate-co-itaconate) and polyol. For proper control of the crosslinking, it is critical that the copolymer starting-material be capable of forming anhydride functionality during the thermal cure. In the case of the poly(arcylate-co-itaconate), the 1,4-diacid functional (present in the copolymer by virtue of itaconate) will dehydrate during heating, to afford the requisite anhydride. Best results can be achieved by operating in specific, acidic pH ranges, and by control of the cation composition, especially by avoiding strongly co-ordinating polyvalent metal ions.

The term "fiber" is used to distinguish the immediate product of the invention from strong interbonded masses of paper fibers. The latter might seem similar based on a mere recital of ingredients, but do not have the dispersability and absorbency properties of the invention.

Thus, as noted, the fiber of the invention can be used on large scale as a papermaking pulp, especially in admixture with conventional papermaking fiber. Paper webs made by wet-laying such pulps are especially useful for making disposable absorbent paper towels having a unique distribution of absorbent material, which are capable of quickly absorbing appreciable amounts of water or watery fluids.

Useful embodiments of the invention include a wet-laid paper web, comprising at least 1% (preferably 5% to 10%) up to about 60% of chemically modified fiber of the invention. Excellent webs are secured when the content of fiber of the invention is from about 20% to about 50%.

The invention also encompasses a disposable absorbent article, such as a disposable absorbent towel or a pad for a catamenial, comprising one or more plies of a wet-laid paper web as described herein.

The invention has several significant advantages. Thus the fiber of the invention leads to wet-laid absorbent paper free from aesthetic negatives in use, such as a tendency to shed particles of absorbent material or such as a tendency to feel slippery and gel-like when wetted. Other advantages include, but are not limited to: simplicity; nonreliance on expensive or toxic metal catalysts during the preparation; the ability to improve the absorbency of "difficult" fibers such as chemithermomechanical pulp fibers (which is very desirable in view of the environmental advantages of such fibers as compared with chemical pulp fibers); and importantly, the ability to provide improved absorbent fibers which better accommodate the stresses of wet-laying paper-making with less tendency to disintegrate or cause wire-blocking or drying difficulties than conventional absorbent polymer-treated fibers.

All percentages herein are by weight and temperatures are ambient (25° C.), unless otherwise specifically noted.

DETAILED DESCRIPTION OF THE INVENTION

Chemical Structure Features—Description of the Drawing

Figure 1:
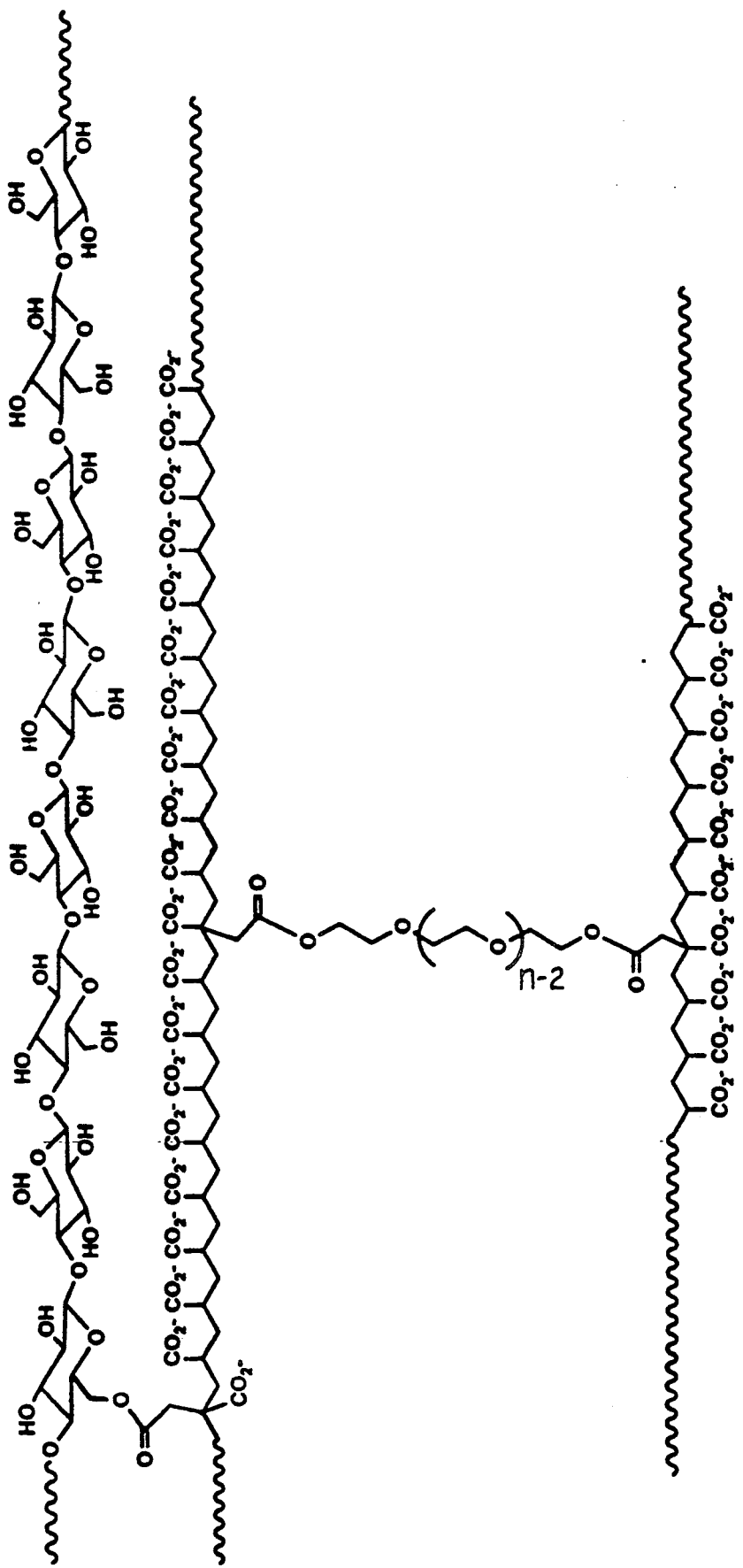
FIG. 1 illustrates the important types of chemical bonding between cellulose, acrylate, itaconate and polyethylene glycol in a fiber according to the invention.

A fiber in accordance with the instant invention is effectively a cellulosic fiber of natural origin to which is chemically attached a lightly crosslinked mixture of particular synthetic components, namely a poly(acrylate-co-itaconate) and a polyol. Without being limited by theory, the essential features of the chemical bonding occurring in a preferred embodiment of the invention are illustrated in FIG. 1.

FIG. 1 shows, covalently bonded together, (i) a cellulose moiety, (ii) itaconate moieties (these form junctions between the other moieties), (iii) polyacrylate moieties and (iv) a polyol moiety, which in FIG. 1 is one derived from a polyethylene glycol. Not shown are the fiber as a whole, of which the depicted cellulose moiety is but a part, as well as cations (sodium being preferred), which are inherently present in a charge-balancing amount and are primarily associated with the negative charges of the copolymer; water molecules; and any imperfections, such as incompletely reacted moieties.

Important features of the invention illustrated in FIG. 1 include that the relative proportion of itaconate to acrylate is low, ensuring a relatively light crosslinking. Moreover, the lightly crosslinked acrylate/itaconate/-polyol structure is chemically attached to the cellulosic fiber.

The fibers of the invention are quite different from grafted cellulosic fibers of well-known kinds which can be made, for example by cerium-catalyzed polymerization of methyl acrylate in presence of a cellulosic fiber followed by sodium hydroxide hydrolysis. A known technique for finding the location of a highly charged synthetic polycarboxylate polymer in relation to a material such as cellulose which is less highly charged involves mapping the distribution of charge-balancing cations, such as sodium, by X-ray Energy Dispersive Spectroscopy. Sodium ion maps of preferred fibers of the invention show substantially intact cellulose regions without high concentrations of sodium being present between the fiber wall and the fiber lumen, whereas there is a significant proportion of sodium distributed between the fiber wall and the lumen in typical hydrolyzed methyl-acrylate grafted fibers.

Without being bound by theory, it is believed that having a fiber with substantially intact cellulosic regions of natural origin and a chemically attached, lightly crosslinked, water-swellable poly(acrylate-co-itaconate are important for securing the benefits of the instant invention.

Composition of fiber of the invention

In general, the fiber of the invention comprises, chemically bonded together: (a) a cellulosic fiber; (b) a poly(acrylate-co-itaconate and (c) a polyol.

(a). Cellulosic Fiber.

The cellulosic fiber, to which the remaining components are bonded in the fiber of the invention, is a conventional material. In general, it is selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood sulfite pulp fiber, unbleached softwood sulfite pulp fiber, cotton linters, mercerized dissolving pulp fiber, unmercerized dissolving pulp fiber, and mixtures thereof.

Preferred cellulosic fiber is selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, and mixtures thereof.

Highly preferred embodiments of the invention include those made from chemithermomechanical pulp fiber and bleached Kraft fiber such as southern softwood Kraft fiber. As will be seen hereinafter, there are somewhat different preferred synthesis conditions, especially relating to pH, curing temperature and curing time, depending on which of these highly preferred fibers is chosen.

Preferably, such fiber will be of a quality deemed good or superior for the purposes of conventionally making wet-laid paper webs. More specifically, fiber having relatively low levels of "fines" and a good staple length are preferred.

(b). Poly(acrylate-co-itaconate).

The fiber of the invention also contains a poly(acrylate-co-itaconate). In general, this copolymer has an acrylate content of from about 50 mole % to about 99 mole %, more preferably about 70 mole % to about 98 mole %, most preferably about 90 mole % to about 95 mole % and an itaconate content of about 1 mole % to about 50 mole %, more preferably about 2 mole % to about 30 mole %, most preferably about 5 mole % to about 10 mole %.

The poly(acrylate-co-itaconate) useful herein are selected members of a known class of copolymers. They may be prepared by conventional, art-known techniques for copolymerizing acrylic acid and itaconic acid. Typically, mild aqueous conditions using a conventional water-soluble free-radical initiator are used. Suitable initiators are illustrated by the common azo initiators such as 2,2'-azobis(2-amidinopropane) dihydrochloride; as well as potassium persulfate, hydrogen peroxide or the like. Selection of a copolymer useful herein is based on a recognition that any given itaconate moiety in the copolymer will be unreactive for the purposes of forming the fiber of the invention if at the time thermal crosslinking is attempted, an itaconic anhydride moiety cannot be formed. Such resistance to forming the anhydride is exhibited especially when the itaconate component of the copolymer is completely neutralized, such as in the form of the diammonium salt, and to an even greater extent, when the itaconate component of the copolymer is co-ordinated with multivalent metal ions such as those of calcium, magnesium or iron. For practical purposes, it is therefore highly preferred both to use the acid form of the copolymer and to limit the content of multivalent metal cations in the copolymer. The latter can best be achieved by synthesizing the copolymer in clean water.

Although isolable, the copolymer can conveniently be made, and further directly used to form the fiber herein, as an aqueous solution.

Copolymers most useful herein have weight average molecular weight, $M_W$, as determined by low angle laser light scattering, in the general range from about 60,000 to about 1,000,000. Preferred copolymer has weight average molecular weight of from about 400,000 to about 1,000,000. Within practical limits, the absorbent properties of the fiber of the invention increase significantly as the weight average molecular weight of the copolymer increases. Since copolymers tend to become viscous and difficult to handle at very high weight average molecular weight, a highly preferred copolymer weight average molecular weight is in the range from about 600,000 to about 900,000.

As found in the fiber of the invention, the copolymer is chemically bonded to the cellulosic fiber and to the polyol.

(c). Polyol

The polyol component of the fiber of the invention is an alcohol having two or more —OH groups. In the fiber of the invention, as illustrated in FIG. 1, the polyol is at least partially chemically incorporated by reaction with itaconic anhydride moieties of the copolymer (see the chemistry of the synthesis further discussed hereinafter) so that it is no longer in the free state and acts as a crosslinking group in the fiber of the invention. Although a wide variety of polyols are useful herein, preferred polyols are water-soluble. Although any polyol consisting essentially of C, H and O can be used, the polyol is typically selected form the group consisting of polyethylene glycol, polyvinyl alcohol, ethylene glycol, propylene glycol, glycerin, pentaerythritol and the like.

Another polyol capable of being substituted for propylene glycol within the spirit and scope of the invention is a relatively longer chain alpha-omega alkylene diol, such as a 1,6 hexylene glycol.

In preferred embodiments, the polyol is a diol, such as polyethylene glycol, and can have varying molecular weight. Suitable diol materials have the formula $HO(CH_2CH_2O)_nH$ wherein n is from about 4 to about 154, more preferably from about 34 to about 100, most preferably from about 70 to about 80. Preferred embodiments of these materials are to be found in the commercial PEG 200-7000 series. Thus, commercial PEG 200 corresponds with n in the above formula of about 4, PEG 1000 corresponds with n of about 22, PEG 1500 corresponds with n of about 34, PEG 3350 corresponds with n of about 76 and PEG 6800 corresponds with n of about 154. In practice, it is found that although quick-wicking fiber of the invention can be prepared with PEG 200, absorbency results are optimal with PEG 3350. PEG 6800, though usable, gives somewhat less preferred embodiments of the invention.

Proportions of components

In general, the proportion by weight of poly(acrylate-co-itaconate) to polyol in the fiber of the invention is in the range from about 250:1 to about 3:1, more preferably from about 30:1 to about 4:1, most preferably from about 10:1 to about 5:1. When the polyol has a low molecular weight, such as ethylene glycol, the weight amount of polyol is relatively low. As the molecular weight increases in a homologous series, such as in PEG of progressively increasing molecular weight, the relative weight of polyol increases. When the polyol has many —OH groups, as in polyvinylalcohols, the relative proportion by weight of polyol may be low, even though the molecular weight of the polyol is high.

Without being limited by theory, it is believed that the proportion of copolymer to polyol is very important for controlling the crosslink density in the fiber of the invention. The above-recited ranges take into account that maintaining a relatively constant, consistently low crosslink density is preferred.

In the fiber of the invention, the add-on, that is to say the weight of poly(acrylate-co-itaconate) plus polyol ((b) plus (c)) per unit weight cellulosic fiber (a) is in the general range from about 0.3 grams per gram to about 2 grams per gram, more preferably from about 0.6 grams per gram to about 1.5 grams per gram, most preferably from about 0.8 to about 1.2 grams per gram. It should be appreciated that as the add-on is progressively decreased, the absorbency of the fiber decreases but the fiber may become somewhat easier to process. On the other hand, excessive add-on, outside the scope of this invention, can lead to an appreciable content of pieces of absorbent polymer which are not chemically attached to the fiber. Moreover, there appears to be a plateau effect of absorbency performance and usefulness when much more than the stated upper limit of add-on is used.

It should be appreciated that add-on levels herein are, in percentage terms, rather high, i.e., 30% to 200%. These levels are very much higher than in conventional paper coatings, wet-strength additive applications or the like.

The poly(acrylate-co-itaconate) weight referred to hereinabove and throughout the specification is by convention expressed on an acid equivalent basis. That is to say, regardless of the form of the poly(acrylate-co-itaconate) used in the synthesis of the fiber of the invention, and equally regardless of the form product fiber, the convention is adopted of everywhere specifying the poly(acrylate-co-itaconate) weight as though it were in the acid form, i.e., all the charge-balancing cations are H. In this manner, the relative proportion of poly(acrylate-co-itaconate) to the cellulose and polyol components is unambiguously determined.

Cations

Since the fiber of the invention contains negatively charged carboxylate groups, especially those associated with the poly(acrylate-co-itaconate) cations will inherently be present in a charge-balancing amount.

In the fiber of the invention, the cations are generally selected from sodium, potassium, lithium, hydrogen and mixtures thereof, more preferably sodium, potassium, hydrogen and mixtures thereof, most preferably sodium, hydrogen and mixtures thereof.

A similar range of cation composition applies to the copolymer starting-material, however the most highly preferred cation for the starting-material copolymer is hydrogen. Thus the starting form of the copolymer is most preferably the acid form.

The fiber of the invention can be in the acid form, in which it is not directly useful as in absorbent material but is very useful for long-term storage or shipping from the fiber manufacturing plant to the papermaking plant at high consistency; or it can be int he highly absorbent sodium form. Other such water-soluble monovalent cation salts of the fiber of the invention, such as the potassium salt, as noted, are likewise useful absorbents.

Importantly, polyvalent cations such as those of iron, calcium, magnesium and aluminum are avoided, both in the starting copolymer and in the fiber of the invention, as much as practical considerations will allow. Such cations can not only interfere with the synthesis of the fiber but also with the absorbent properties of the product fiber.

Absorbency property

The fiber of the invention is most useful as an absorbent material. Thus, it has a water absorbency and retention value (WAARV)—this quantity being measured according to the procedure given in "Test Methods" hereinafter—in the range from about 15 g/g to about 130 g/g, more preferably from about 30 g/g to about 100 g/g, most preferably from about 50 g/g to about 90 g/g.

The term "retention" in WAARV takes into consideration that the test method involves centrifugation, so that water quite tenaciously retained by fiber, pulp or paper is included in the absorbency measurement. Moreover, WAARV values are measured at a constant alkaline pH so that values are reproducible and can be compared. WAARV can be used to characterize both acid-form and salt-form fibers according to the invention because during the test, in-situ conversion of acid-form to salt-form fiber takes place. Moreover, WAARV can be used to measure the absorbency of wet-laid webs comprising the fiber of the invention.

Without being bound by theory, it is believed to be important that the fiber herein is substantially discrete rather than a mass of strongly interbonded fibers with significant amounts of polymer located at the fiber crossovers. That latter behavior, believed inferior for absorbency purposes, is the kind to be expected when the fiber results from (i) forming paper, e.g., on a Fourdrinier wire then (ii) applying a polymer, for example by spray-on or impregnation, then (iii) crosslinking the polymer: such a sequence is not in accordance with this invention.

Thus the fiber of the instant invention results from (i) concentrating the polymer components as much as possible on individual cellulosic fibers prior to making paper, then (ii) thermally crosslinking to form the chemical bonds between the polyol-copolymer mixture and the fiber. The resulting fiber can then (iii) be used in bulk as a papermaking pulp or furnish for wet-laying to achieve an absorbent, quick-wicking paper web free from aesthetic disadvantages.

Chemistry of Synthesis

It should be understood that water ($H_2O$) is eliminated in the chemical reactions of curing or thermally crosslinking which are normally used to form the fiber of the invention. Without being limited by theory, the following chemical reactions are believed to occur:

(I) all or at least part of the itaconate moieties of the copolymer dehydrate in the presence of heat to give itaconic anhydride moieties;

(II) a portion of the itaconic anhydride moieties further react by acylating the —OH groups of the cellulosic fiber, (a): this results in at least partial chemical attachment of copolymer to fiber via covalent ester bonds of cellulose to itaconate; and (III) a portion of the itaconic anhydride moieties further react by acylating the —OH groups of the polyol: since the polyol is at least difunctional, this results in crosslinking of the copolymer and polyol.

Although it is believed that substantially all itaconate moieties are accounted for by participating in reaction (II) or (III), it is normal practice herein to provide a slight excess of itaconate moieties beyond that required for complete reaction. Thus the fiber of the invention may contain traces of non-crosslinked itaconate and, although unlikely, it is believed that traces of anhydride-form itaconate may be present in dry fiber of the invention.

To be noted is that the terms "curing", "thermally crosslinking", "crosslinking" and "chemically reacting" are equivalent herein, at least inasmuch as they refer more or less specifically to producing the fiber of the invention. Curing temperatures and times are very important and are discussed at length hereinafter.

Preparation of fiber of the invention

In general, fiber of the invention can be made by lightly crosslinking, typically by a thermal method, a cellulosic fiber of a quality suitable for wet-laying papermaking, typically a conventional wet-laying papermaking fiber such as bleached southern softwood Kraft or chemithermomechanical fiber, with an intimate mixture of poly(acrylate-co-itaconate) and polyol.

It is essential that immediately prior to thermal crosslinking, the poly(acrylate-co-itaconate) should be capable of producing an acidic solution in water, for the simple reason that the fully neutralized salts, such as the diammonium salt, the disodium salt etc., are incapable of thermally eliminating water and of forming an anhydride, which as discussed supra, is an essential part of the chemical reaction leading to the fiber of the invention.

It is consistent with the sense of the invention to deposit copolymer-polyol mixtures on cellulosic fibers using a process such as extrusion, evaporative deposition or any similar deposition method, regardless of whether it involves a fluid medium or carrier or not.

When there is no medium to be removed, the mixed fiber/copolymer/polyol can be directly crosslinked by heating at suitable curing temperatures for limited curing times, always provided that a suitably intimate mixture has been formed.

When it is desired to make fibers without resorting to expensive process equipment, a medium can be used to deposit the poly(acrylate-co-itaconate) on the starting-material cellulosic fiber. In this event, the medium should preferably be capable of substantially completely dissolving the poly(acrylate-co-itaconate) and the polyol, so that an intimate mixture of the two can be evaporatively deposited on the cellulosic fiber. The medium should be capable of substantially complete evaporation at normal or reduced pressures below the temperatures at which thermal crosslinking occurs. Acetone/water mixtures, acetone/water/methanol, mixtures, and methanol/water mixtures are all quite suitable, as are water mixtures with other common low-boiling water-miscible organic solvents, but water alone is highly preferred, especially on account of low cost and low toxicity.

When water dissolves the poly(acrylate-co-itaconate) and polyol, the result is an "aqueous medium" for the purposes of this invention. Typically, the aqueous medium has a percentage by weight of poly(acrylate-co-itaconate) plus polyol which is about 10% by weight or higher, more preferably the concentration is about 20%. Much more importantly, the aqueous medium is found to behave quite differently, in terms of its suitability, depending on the pH. In general, the pH of the aqueous medium must lie in the range from about 1.8 to about 4.0, more preferably from about 2.5 to about 3.5. When the cellulosic fiber to be treated is chemithermomechanical fiber, a pH range of from about 1.8 to about 4.0 is acceptable. When other cellulosic fiber types are being treated, it is essential that the pH of the aqueous medium should be in the range from about 2.5 to about 4.0. Below the above-specified pH minima, depending on the precise type of cellulosic fiber, the cellulosic fiber will tend to degrade. Moreover, at pH values much above pH the stated upper limit, the degree of crosslinking in the crosslinking step is sharply reduced, to an unacceptable extent.

Water used to make the aqueous medium is preferably substantially free from polyvalent cations such as those of calcium, magnesium, iron and aluminum. In any event, the content of such cations should not be so high as to inhibit the thermal crosslinking reaction.

Once the poly(acrylate-co-itaconate) and polyol are dissolved and an aqueous medium is formed, the medium can be applied to cellulosic fibers in whatever manner desired, provided that these fibers are discrete or dispersed rather than knit together in the form of a bonded web.

The mixture of cellulosic fibers and aqueous medium is evaporated at non-crosslinking temperatures. For practical purposes, such temperatures are generally below about 75° C., typically in the range 50° C. to 70° C. At higher temperatures, there is an increased risk of uncontrolled crosslinking. Lower temperatures can be used: for example water can be evaporated by freeze-drying.

Evaporation of water results in a substantially dry, intimate mixture of the poly(acrylate-co-itaconate) and polyol on the cellulosic fibers.

Preferably, the evaporation is carried out under conditions which avoid sticking together of the fibers. One suitable approach believed to be good for removing water from the aqueous medium and uniformly deposition the poly(acrylate-co-itaconate) and polyol as an intimate mixture on the cellulosic fiber surface involves the use of a supercritical fluid such as supercritical carbon dioxide for extracting the water.

A preferred approach to the depositing operation which has been found quite satisfactory, especially on grounds of economy and simplicity, is to evaporate a thin layer of the poly(acrylate-co-itaconate)/polyol/fiber/water mixture. Although there may be some sticking together of fibers, the evaporated layer is readily repulped (after the crosslinking step described in detail below) to give substantially discrete fibers of the invention.

In general, crosslinking or "curing" herein involves applying a controlled amount of heat, which can be achieved under a range of temperatures and times.

Thus, in a preferred embodiment, the invention encompasses a process for preparing a chemically modified fiber having a water absorbency and retention value in the above-recited ranges, comprising a step of:

thermally crosslinking, at a curing temperature of from about 100° C. to about 150° C., more preferably from about 110° C. to about 140° C. for a curing time of from about 60 minutes to about 2 minutes, more preferably from about 33 minutes to about 3 minutes, a starting material pulp consisting essentially of the above-identified cellulosic fiber (component (a)); with an intimate mixture of poly(acrylate-co-itaconate) (above-identified as (b), and a polyol (component (c) identified hereinabove); wherein the proportion by weight of poly(acrylate-co-itaconate) copolymer to polyol is in the above-recited general ranges and the weight of poly(acrylate-co-itaconate) plus polyol per unit weight of cellulosic fiber, (a), is likewise as recited hereinabove.

In practice, the copolymer-polyol treated dry cellulosic fibers are preferably exposed to heat as a thin layer. Preferably, a pre-heated oven is used for best control of the crosslinking or curing reaction. In order to minimize curing time at any given curing temperature, the practitioner will preferably use a flow of hot air and will permit access of the hot air to both sides of the fiber layer by first removing any substrate which may have been used in the above-described fiber-polymer contacting procedures: in practice, this is most easily accomplished when the substrate is "non-stick", for example, polytetrafluoroethylene (PTFE).

Based on this appreciation of the curing operation, the practitioner will readily appreciate that it is possible to conduct evaporative deposition and thermal crosslinking, indeed the entire synthesis of the fiber of the invention, in a continuous or semi-continuous mode. For example, a PTFE carrier belt can carry the cellulosic fiber, copolymer and polyol through the evaporative deposition stage and into the curing stage in the synthesis process.

It is however been found that it is preferred to cure in the absence of a substrate, or in the presence of a substrate which does not overly affect heat flow into the above-described thin layer during curing.

Thus, when curing a fiber/copolymer/polyol layer about 1 mm thick on glass about 3 mm thick, the layer being one resulting from evaporation of an aqueous medium having a pH of 3.00, the following curing temperatures and the corresponding curing times are illustrative of preferred curing conditions:

| Curing Temperature (°C.) | Curing Time (minutes) |
|---|---|
| 110 | 33 |
| 120 | 18 |
| 130 | 11.5 |
| 140 | 8 |

In the above and throughout the specification, curing times are defined as the total period of exposure to hot air at the curing temperature, the fiber layer being introduced to the hot air oven at ambient temperature.

Substituting PTFE for glass as a substrate for evaporating the aqueous medium in the above, and removing the PTFE from a layer now about 2 mm thick prior to curing, a preferred curing time at a temperature of 130° C. is reduced from 11.5 minutes (glass-see the above) to about 6.5 minutes (no substrate). The reduction in the curing time is believed to be due to the improved access of hot air to both sides of the fibrous layer.

In light of the above, the practitioner should be aware that for best results, especially when manufacturing on a large scale, it is advisable to optimize the curing temperature and time at the scale chosen, by the simple expedient of measuring Fiber Yield and water absorbency and retention values of the fiber of the invention, each as defined in "Test Methods" hereinafter, over a series of curing temperatures and times in accordance with the invention.

Once curing is complete, the raw fiber of the invention is repulped, preferably with an amount of shear which will not significantly reduce the staple. Repulping is generally carried out in water under acid conditions, typically at a pH of about 2 to about 4, more preferably at pH of about 2 to about 3 (hence the term "acid repulping" can be used to characterize this step). In the acid repulping step, the fiber of the invention is substantially in the acid form. In this form, the fiber is non-swollen and is readily manipulated, thus in this form it has the advantage that it can conveniently be shipped as a concentrated slurry from the fiber manufacturing plant to the papermaking plant if desired.

After repulping, the fiber of the invention can be secured substantially in the dry, sodium-salt form by a fiber-swelling step. The fiber-swelling step simply involves neutralizing with sodium hydroxide, preferably to a pH of from about 7.5 to about 9, whereon the fiber swells greatly. The fiber swelling step can be quite slow, and may take up to 2-3 days. It is a curious feature of the fiber of the invention that the first conversion from the acid form to the sodium salt form is of such duration, since subsequent interconversions between the acid and salt forms can be carried out quite rapidly by adding acid or base, as needed.

If desired, after the fiber-swelling step, the fiber of the invention can be filtered and dried, typically at temperatures of about 80° C.-90° C., although this is not necessary and is not usually practiced if the fibers are to be used as a pulp for wet-laying papermaking.

To be noted is that fibers of the invention in the sodium salt form are superior in their heat resistance as compared with the corresponding fibers in the acid form. If in the above, the sodium hydroxide is substituted by potassium hydroxide or lithium hydroxide, the corresponding potassium and lithium salt forms of the fiber of the invention can be secured.

For the practical reason that the fiber of the invention is typically used in a wet-laying process, the practitioner generally does need to dry the salt form of the fiber prior to use in wet-laying, but can directly use it as a slurry.

Webs and Wet-Laying Processes for their Production

In other embodiments, the invention provides a wet-laid paper web comprising from about 5% to about 60%, more preferably from about 10% to about 60%, most preferably from about 20% to about 50% of the fiber of the invention (or equivalently, the product of the above-identified synthesis process). The balance of the composition can be conventional papermaking fibers, such as fibers having an identical composition to the starting-material fibers. When mixtures of fiber of the invention and conventional papermaking fibers are co-distributed in a wet-laid web, highly absorbent, quick-wicking structures result.

Preferred papermaking processes useful herein, as incorporated by reference in the background art discussion hereinabove, include continuous wet-laying processes designed for making conventional highly absorbent paper.

A feature of interest which distinguishes several such processes and is believed to be useful in the context of the present invention is to avoid compressing or squeezing (e.g., calendering) the wet-laid web as much as possible during drying; also, it can be helpful to dry the webs containing the fiber of the invention using blow-through air dryers of conventional construction. This produces a rather open, absorbent web.

A modification of a conventional wet-laying process which is especially helpful for making wet-laid webs according to the present invention in a continuous operation simply involves wet-laying at acidic pH, typically in the range from about 3 to about 5, followed by partially drying the wet-laid web, neutralizing on-line with a sprayed-on sodium carbonate or potassium carbonate solution (sodium hydroxide may be used but can yellow the web is not carefully applied), and drying, especially with the aid of a conventional Yankee dryer.

Disposable absorbent towels

The wet-laid webs can be used as plies in a two-ply or multi-ply disposable absorbent structure such as a disposable absorbent towel. All that needs to be done to secure such disposable absorbent structures is to combine plies comprising at least one wet-laid paper web according to the invention, in a conventional converting operation, e.g., simple glueing or bonding of the plies together.

ALTERNATE EMBODIMENTS OF THE INVENTION

The fiber of the invention is not limited to use as an absorbent for disposable absorbent towels, but may be used for making catamenial pads, absorbent dressings, pantiliners and the like.

Fibers in accordance with the invention are further illustrated by the following Examples.

EXPERIMENTAL

Starting-materials

Acrylic acid (Polysciences Inc., Warrington, Pa.) is vacuum distilled through a Vigreux column and is preferably used fresh in subsequent operations, e.g., within one day of distillation. Itaconic acid (Aldrich Chemical Co., Milwaukee, Wis.) is obtained in 99%+purity and is used as received. The free-radical initiator 2,2'-azobis(2-amidinopropane) dihydrochloride (WAKO V-50, Wako Pure Chemical Industries, Osaka, Japan) is also used as received. Unless otherwise noted, water is triply distilled. Where polymers are dialyzed, the dialysis membrane is obtained from Spectrum Medical Industries, Inc., Los Angeles, Calif.

Polyethylene glycols (these preferred polyols are commonly known as "PEG", various suppliers being suitable) as used in the Examples have nominal molecular weights of 200, 1000, 1500, 3350, and 6800. PEG 200 is obtained from Polysciences Inc., Warrington, Pa. PEG 1000, PEG 1500 and PEG 6800 are obtained from Scientific Polymer Products, Inc., Ontario, N.Y. PEG 3350 is obtained from Sigma Chemical Co., St. Louis, Mo.

Southern softwood Kraft pulp and northern softwood Kraft pulp are obtained from P & G Cellulose, Memphis, Tenn. Chemithermomechanical pulp is obtained from Quesnel Paper Co., Quesnel, B.C., Canada.

EXAMPLE I

Preparation of an poly(acrylate-co-itaconate) suitable for use in making fiber of the invention (90 mole % acrylate, 10 mole % itaconate)

Acrylic acid (20.000 g, 0.27755 mole), itaconic acid (4.0121 g, 0.038386 mole), Wako V-50 (0.0837 g, 0.308 millimole), and 150 ml of water which has been acidified to pH 2.0 with hydrochloric acid are added to a 250 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 55° C. and is maintained at this temperature for 15 hours. The viscous solution of copolymer is cooled to ambient temperature and is dialyzed overnight against water (Spectrapor 3 tubing with molecular weight cut-off at 3500) to remove any unreacted monomers. The dialyzed solution is freeze dried to afford 23.00 g of poly(acrylate-co-itaconate), acid form, as a colorless solid. The weight average molecular weight, $M_W$, as determined by low angle laser light scattering in 0.2 Molar sodium chloride in water (refractive index = 1.3344, $d_n/d_c$ = 0.1683) is 896,100.

EXAMPLE II

Preparation of another poly(acrylate-co-itaconate) suitable for making fiber of the invention (90 mole % acrylate, 10 mole % itaconate)

Acrylic acid (25.000 g, 0.34693 mole), itaconic acid (5.0151 g, 0.038548 mole), Wako V-50 (0.1046 g, 0.3856 millimole), and 193 ml of water which has been acidified to pH 2.0 with hydrochloric acid are added to a 500 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 60° C. and is maintained at this temperature for 15 hours. The viscous solution of copolymer is cooled to ambient temperature and is dialyzed against distilled water overnight (Spectrapor 3 tubing as in the foregoing Example) to remove any unreacted monomers. The dialyzed solution is freeze dried to afford 28.31 g of poly(acrylate-co-itaconate), acid form, as a colorless solid. The weight average molecular weight, $M_W$, as determined by low angle laser light scattering in 0.2 Molar sodium chloride in water (refractive index = 1.3344, $d_n/d_c$ = 0.1683) is 658,200.

EXAMPLE III

Preparation of another poly(acrylate-co-itaconate) suitable for making fiber of the invention (90 mole % acrylate, 10 mole % itaconate)

Acrylic acid (105.27 g, 1.4609 moles), itaconic acid (21.12 g, 0.1623 mole), Wako V-50 (0.4403 g, 1.623 millimole), and 812 ml of water which has been acidified to pH 2.0 with hydrochloric acid are added to a 2 liter three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 55° C. and maintained at this temperature for 15 hours. The viscous solution of copolymer is cooled to ambient temperature, and is freeze dried to give 121.57 g of poly(acrylate-co-itaconate), acid form, as a colorless solid. The weight average molecular weight, $M_W$, as determined by low angle laser light scattering on a dialyzed portion in 0.2 Molar sodium chloride in water (refractive index = 1.3344, $d_n/d_c$ = 0.1683) is 821,600.

EXAMPLE IV

Preparation of another poly(acrylate-co-itaconate) suitable for making fiber of the invention (90 mole % acrylate, 10 mole % itaconate)

Acrylic acid (1050.0 g, 14.571 moles), itaconic acid (210.64 g, 1.6190 moles), Wako V-50 (4.3919 g, 16.19 millimole), and 7.9 liters of water which has been acidified to pH 2.0 with hydrochloric acid are added to a 22 liter three-necked round-bottomed flask fitted with a thermometer, a mechanical stirrer, and gas inlet/outlet adapter capable of bubbling gas through a liquid in the flask and venting it. The solution is deaerated by passage of nitrogen gas and is then placed under an atmosphere of nitrogen. The solution is heated to 55° C. and maintained at this temperature for 15 hours. The viscous solution of copolymer is cooled to ambient temperature and is freeze dried to give 1,222.1 g of poly(acrylate-co-itaconate), acid form, as a colorless solid. The weight average molecular weight, $M_W$, as determined by low angle laser light scattering on a dialyzed portion in 0.2 Molar sodium chloride in water (refractive index = 1.3344, $d_n/d_c$ = 0.1683) is 711,700.

EXAMPLE V

Preparation of another poly(acrylate-co-itaconate) suitable for making fiber of the invention (95 mole % acrylate, 5 mole % itaconate)

Acrylic acid (25.00 g, 0.3469 mole), itaconic acid (2.376 g, 18.27 millimole), Wako V-50 (0.0991 g, 0.365 millimole), and 183 ml of water which as been acidified to pH 2.0 with hydrochloric acid are added to a 500 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 55° C. and maintained at this temperature for 15 hours. The viscous solution of copolymer is cooled to ambient temperature and is dialyzed against distilled water overnight (Spectrapor 3 tubing as in the foregoing Examples) to remove any unreacted monomers. The dialyzed solution is freeze dried to afford 25.99 g of poly(acrylate-co-itaconate), acid form, as colorless solid. The weight average molecular weight, $M_W$, as determined by low angle laser light scattering in 0.2 Molar sodium chloride in water (refractive index = 1.3344, $d_n/d_c$ = 0.1683) is 683,900.

EXAMPLE VI

Preparation of another poly(acrylate-co-itaconate) copolymer suitable for making fiber of the invention (95 mole % acrylate, 5 mole % itaconate)

Acrylic acid (21.11 g, 0.2930 mole), itaconic acid (2.0061 g, 15.420 millimole), Wako V-50 (0.0837 g, 0.309 millimole), and 150 ml of water which has been acidified to pH 2.0 with hydrochloric acid are added to a 250 ml three-necked round-bottomed flask. The necks are fitted with a thermometer, a stopper, and a gas inlet/outlet adapter capable of bubbling gas through a liquid in the flask and venting it. The solution is deaerated by passage of nitrogen gas and is then placed under an atmosphere of argon. The solution is heated to 55° C. and maintained at this temperature for 15 hours. The viscous solution of copolymer is cooled to ambient temperature and a portion is dialyzed against distilled water overnight (Spectrapor 3 tubing as in the foregoing Examples) to remove any unreacted monomers and then freeze dried to afford 1.5 g of poly(acrylate-co-itaconate), acid form, as a colorless solid. The remainder of the solution is diluted with water to give a 12% solids content and is used directly, without drying, in the synthesis of fibers in accordance with the invention. The weight average molecular weight, $M_W$, as determined by low angle laser light scattering on the dialyzed portion in 0.2 Molar sodium chloride in water (refractive index = 1.3344, $d_n/d_c = 0.1670$) is 925,000.

EXAMPLE VII

Preparation of fiber of the invention

Poly(arcylate-co-itaconate) of EXAMPLE III (2.00 g) is dissolved by adding it portionwise to 20 ml of water while stirring and heating to 65°-70° C. To the solution is added polyethylene glycol (0.334 g, nominal molecular weight 3350) predissolved in 5 ml of water. Stirring is continued until dissolution is complete. The resulting aqueous medium is cooled to ambient temperature and the pH is adjusted to 3.00 (the "pH of the aqueous medium" referred to elsewhere herein) with 1 Molar sodium hydroxide. Loose fibers of southern softwood Kraft pulp (2.00 g bone-dry weight basis) are added. The resulting slurry is thoroughly mixed and is spread out into a thin layer on a 6-inch diameter watch glass of thickness about 3 mm. The slurry layer is dried in an oven at 65°-70° C., a temperature selected to minimize or avoid crosslinking reactions, and is then cured by placing the watch glass in an oven preheated to a curing temperature of 130° C. The curing time is 11.5 minutes. The layer, now about 1 mm thick, is cooled to ambient temperature. This yields fiber in the acid form, which is not particularly absorbent. The fiber is then repulped. In practice it is convenient to soak it with distilled water, tear it into small pieces and add it to 400 ml of distilled water. After further stirring (e.g., overnight) the pH of the mixture is adjusted to 2.0 with hydrochloric acid and it is mixed in a Waring Blendor in two steps wherein (1) the blendor is run on low speed for 5.0 minutes at 50% power and (2) the blendor is run for 1.0 minute on low speed at full power. The fibers, still in the acid form, are collected by suction filtration in a Buchner funnel fitted with a handsheet forming wire, washed the 400 ml of water, and are re-suspended into 500 ml of water. The slurry pH is adjusted to 8.5 using 1 Molar sodium hydroxide in water. (Using potassium hydroxide or lithium hydroxide instead of sodium hydroxide at this stage would result in the potassium or lithium form of the fibers.) Over two days, the pH is periodically checked and readjusted to 8.5 with sodium hydroxide. During this period, the fibers exchange to the sodium salt form, which is highly absorbent. Thus, the fibers swell up. The fully swollen fibers of the invention are collected by suction filtration and are washed with distilled water. Their wet weight is 232.62 g and their consistency (Test Method given hereinafter) is determined to be 1.656%, from which the Fiber Yield (Test Method given hereinafter) is calculated to be 3.85 g of fiber of the invention. The Conversion (Test Method given hereinafter) is calculated as about 89%. The WAARV of the fiber of this Example (Test Method given hereinafter) is determined as 96.3 g/g.

EXAMPLE VIII

Preparation of fiber of the invention

Poly(acrylate-co-itaconate) of EXAMPLE IV (25.00 g) is dissolved by adding it portionwise to 250 ml of water while stirring and heating to 65°-70° C. To the solution is added polyethylene glycol (4.1667 g, nominal molecular weight 3350) predissolved in 15 ml of water. Stirring is continued until dissolution is complete. The resulting aqueous medium is now cooled to ambient temperature and the pH is adjusted to 3.00 with 1 Molar sodium hydroxide. Loose fibers of southern softwood Kraft pulp (25.00 g bone-dry weight basis) are added and the resulting slurry is mixed thoroughly after each portion of pulp is added. The slurry is spread out as a thin, 15-inch by 11-inch layer on a suitably sized polytetrafluoroethylene (TEFLON) sheet. The layer is dried in an oven at 65°-70° C., a temperature selected to minimize or avoid crosslinking reactions, and is then cured by removing it from the TEFLON (for better air-flow) and placing it into an oven, preheated to a curing temperature of 130° C. The curing time is 6.5 minutes. This yields a layer about 2 mm thick of acid-form fiber. This is broken into small pieces and is added to 3 liters of distilled water. After further stirring (e.g., overnight) the pH of the mixture is adjusted to 2.0 with 6 Molar hydrochloric acid and it is mixed in a Waring Blendor in two steps wherein (1) the blendor is run on low speed for 20 minutes at 50% power and (2) the blendor is run for 2.5 minutes on low speed at full power. The acid-form fibers are collected by suction filtration in a Buchner funnel fitted with a handsheet forming wire and washed with 3 liters of distilled water and are re-suspended in another 4 liter aliquot of distilled water. The slurry pH is adjusted to 6.5 using 1 Molar sodium hydroxide in water. The fibers exchange sodium for hydrogen, at least sufficiently to be absorbent. The fibers swell up relatively quickly as compared with Example VII. The pH is periodically re-adjusted to 6.5 with sodium hydroxide over 1 day as the fibers swell. The fibers are collected by suction filtration and are washed with distilled water. Their wet weight is 3564.5 g and their consistency is determined to be 1.43%, from which the Fiber Yield is calculated to be 51.0 g of dry fiber of the invention. The form is absorbent, though not necessarily 100% of the cations inherently present are sodium: there may be hydrogen cations present. The Conversion is about 94%. The WAARV of the fiber is determined as 94.8 g/g.

EXAMPLE IX

Preparation of fiber of the invention

The procedure of Example VII is repeated except that the curing time is 11.0 minutes. The procedure yields fibers having a wet weight of 234.0 g and consistency of 1.755%, from which the Fiber Yield is calculated to be 4.11 g. The conversion is about 95%. The WAARV of the fiber is determined to be 86.8 g/g.

EXAMPLE X

Preparation of fiber of the invention

The procedure of Example VII is repeated except that the poly(arcylate-co-itaconate) is the product of Example I, the cellulosic fiber is chemithermomechanical pulp and the curing time at 130° is 10.0 minutes. The procedure yields fibers having a wet weight of 170.92 g and consistency of 2.58%, from which the Fiber Yield is calculated to be 4.40 g. The Conversion is about 102% conversion. (percentage in excess of 100% is a consequence of expressing starting-material poly(acrylate-co-itaconate) on an acid basis whereas the product contains additional sodium ions). The WAARV is determined to be 79.6 g/g.

EXAMPLE XI

Preparation of fiber of the invention

The procedure of Example VII is repeated except that poly(acrylate-co-itaconate) from example I (1.00 g) dissolved in 10 ml of water, polyethylene glycol with a nominal molecular weight of 3350 (0.150 g), and chemithermomechanical pulp (1.00 g on a bone-dry basis) are used. The pH of the aqueous medium is 2.00 and the curing time is 14.0 minutes at a curing temperature of 130° C. The acid-form fibers are repulped in a Waring Blendor for 1 minute on low speed. The procedure yields fibers having a wet weight of 130.24 g and consistency of 1.59%, from which the Fiber Yield is calculated to be 2.07 g. The Conversion is about 96%. The WAARV is determined to be 51.7 g/g.

EXAMPLE XII

Preparation of fiber of the invention

The procedure of Example VII is repeated with the following exceptions: poly(acrylate-co-itaconate) is from Example V; the starting-material cellulosic fiber is chemithermomechanical pulp; the pH of the aqueous medium is 2.00; and the curing time is 15.0 minutes at a curing temperature of 130° C. After curing, the acid-form fibers are repulped in a Waring Blendor for 1 minute on low speed. The procedure yields fibers having a wet weight of 181.56 g and consistency of 2.09%, from which the Fiber Yield is calculated to be 3.79 g. The Conversion is about 88%. The WAARV is determined to be 46.1 g/g.

EXAMPLE XIII

Preparation of fiber of the invention

The procedure in Example VII is repeated with the following exceptions: poly(acrylate-co-itaconate) is from Example V; the cellulosic fiber used as starting-material is chemithermomechanical pulp, and the curing time at 130° C. is 10.0 minutes. After curing, the acid-form fibers are repulped in a Waring Blendor for 1 minute on low speed. The procedure yields fibers having a wet weight of 205.93 g and consistency of 1.83%, from which the Fiber Yield is calculated to be 3.77 g. The Conversion is about 87%. The WAARV is determined to be 77.2 g/g.

EXAMPLE XIV

Preparation of fiber of the invention

The procedure in Example VII is repeated with the following exceptions: poly(acrylate-co-itaconate) is from Example V and the curing time at 130° C. is 10.0 minutes. After curing, the acid-form fibers are repulped in a Waring Blendor for 1 minute on low speed. The procedure yields fibers having a wet weight of 238.86 g and consistency of 1.72%, from which the Fiber Yield is calculated to be 4.11 g. The Conversion is about 96%. The WAARV is determined to be 97.8 g/g.

EXAMPLE XV

Preparation of fiber of the invention

The procedure in Example VII is repeated with the following exceptions: poly(acrylate-co-itaconate) is from Example VI (16.67 g of the 12% solids solution are used); the cellulosic fiber used as starting-material is chemithermomechanical pulp; the pH of the aqueous medium is 2.00; and the curing time at 130° C. is 14.0 minutes. After curing, the acid-form fibers are repulped in a Waring Blendor for 1 minute on low speed. The procedure yields fibers having a wet weight of 230.0 and consistency of 1.61%, from which the Fiber Yield is calculated to be 3.71 g. The Conversion is about 86%. The WAARV is determined to be 97.8 g/g.

EXAMPLE XVI

Preparation of fiber of the invention

The procedure in Example VII is repeated with the following exceptions: poly(acrylate-co-itaconate) is from Example VI (16.67 g of the 12% solids solution are used); the cellulosic fiber used as starting-material is chemithermomechanical pulp; and the curing time at 130° C. is 10.0 minutes. The procedure yields fibers having a wet weight of 230.52 g and consistency of 1.76%, from which the Fiber Yield is calculated to be 4.06 g. The Conversion is about 94%. The WAARV is determined to be 82.6 g/g.

EXAMPLE XVII

Preparation of fiber of the invention

The procedure of Example VII is repeated with the following exceptions: poly(acrylate-co-itaconate) is from Example II and the curing time at 130° C. is 11.0 min. The procedure yields fibers having a wet weight of 266.02 g and consistency of 1.455%, from which the Fiber Yield is calculated to be 3.87 g. The Conversion is about 89%. The WAARV is determined to be 99.4 g/g.

EXAMPLE XVIII

Preparation of fiber of the invention

The procedure of Example VII is repeated with the following exceptions: poly(acrylate-co-itaconate) is from Example II and the curing time at 130° C. is 12.0 min. The procedure yields fibers having a wet weight of 120.73 g and consistency of 3.81%, from which the Fiber Yield is calculated to be 4.60 g. The Conversion is about 106%. The WAARV is determined to be 62.8 g/g.

EXAMPLE XIX

Preparation of fiber of the invention

The procedure of Example VII is repeated with the following exceptions: poly(acrylate-co-itaconate) is from Example II and the curing time at 130° C. is 13.0 min. The procedure yields fibers having a wet weight of 101.06 g and consistency of 4.53%, from which the Fiber Yield is calculated to be 4.57 g. The Conversion is about 106%. The WAARV is determined to be 49.2 g/g.

EXAMPLE XX

Preparation of fiber of the invention

The procedure of Example VII is repeated with the following exceptions: poly(acrylate-co-itaconate) is from Example II and the curing time at 130° C. is 14.0 min. The procedure yields fibers having a wet weight of 110.12 g and consistency of 4.19%, from which the Fiber Yield is calculated to be 4.61 g. The Conversion is about 106%. The WAARV is determined to be 43.2 g/g.

EXAMPLE XXI

Preparation of fiber of the invention

The procedure of Example VII is repeated with the exception that the pH of the aqueous medium is 2.5. The procedure yields fibers having a wet weight of 314.51 g and consistency of 1.164%, from which the Fiber Yield is calculated to be 3.66 g. The Conversion is about 85%. The WAARV is determined to be 125.8 g/g.

EXAMPLE XXII

Preparation of fiber of the invention

The procedure of Example VII is repeated with the exception that the pH of the aqueous medium is 3.5. The procedure yields fibers having a wet weight of 110.99 g and consistency of 3.955%, from which the Fiber Yield is calculated to be 4.39 g. The Conversion is about 100%. The WAARV is determined to be 17.8 g/g.

EXAMPLE XXIII

Preparation of fiber of the invention

The procedure of Example VII is repeated except that the pH of the aqueous medium is 4.0. The procedure yields fibers having a wet weight of 185.36 g and consistency of 2.25%, from which the Fiber Yield is calculated to be 4.17 g. The Conversion is about 96%. The WAARV is determined to be 43.1 g/g.

EXAMPLE XXIV

Preparation of fiber of the invention

The procedure of Example VII is repeated with the exception that polyethylene glycol with a nominal molecular weight of 200 (0.060 g) is used as the polyol. The procedure yields fibers having a wet weight of 128.57 g and consistency of 2.88%, from which the Fiber Yield is calculated to be 3.71 g. The Conversion is about 91%. The WAARV is determined to be 21.9 g/g.

EXAMPLE XXV

Preparation of fiber of the invention

The procedure of Example VII is repeated except that polyethylene glycol with a nominal molecular weight of 1000 (0.100 g) is used as the polyol. The procedure yields fibers having a wet weight of 228.00 g and consistency of 1.56%, from which the Fiber Yield is calculated to be 3.56 g. The Conversion is about 87%. The WAARV is determined to be 50.8 g/g.

EXAMPLE XXVI

Preparation of fiber of the invention

The procedure of Example VII is repeated except that polyethylene glycol with a nominal molecular weight of 1500 (0.150 g) is used as the polyol. The procedure yields fibers having a wet weight of 211.74 g and consistency of 1.85%, from which the Fiber Yield is calculated to be 3.91 g. The Conversion is about 94%. The WAARV is determined to be 83.7 g/g.

EXAMPLE XXVII

Preparation of fiber of the invention

The procedure of Example VII is repeated except that polyethylene glycol with a nominal molecular weight of 6800 (0.500 g) is used as the polyol. The procedure yields fibers having a wet weight of 138.48 g and consistency of 2.87%, from which the Fiber Yield is calculated to be 3.98 g. The Conversion is about 88%. The WAARV is determined to be 76.8 g/g.

EXAMPLE XXVIII

Preparation of fiber of the invention

The procedure of Example VII is repeated with the following exceptions: poly(acrylate-co-itaconate) copolymer is from Example II (1.00 g dissolved in 20 ml of water); the polyol is polyethylene glycol with a nominal molecular weight of 3350 (0.100 g); the starting-material cellulosic fiber is chemithermomechanical pulp (2.00 g on a bone-dry basis); the pH of the aqueous medium is 2.00 and the curing time at 130° C. is 14.0 minutes. After curing, the fibers are repulped in a Waring Blendor for 1 minute on low speed. The procedure yields fibers having a wet weight of 115.30 g and consistency of 2.54%, from which the Fiber Yield is calculated to be 2.93 g. The Conversion is about 95%. The WAARV is determined to be 24.1 g/g.

EXAMPLE XXIX

Preparation of fiber of the invention

The procedure of Example VII is repeated with the following exceptions: poly(acrylate-co-itaconate) is from Example II (1.80 g dissolved in 30 ml of water); the polyol is polyethylene glycol with a nominal molecular weight of 3350 (0.300 g); the starting-material cellulosic fiber is chemithermomechanical pulp (3.00 g on a bone-dry basis); the pH of the aqueous medium is 2.00 and the curing time at 130° C. is 14.0 minutes. After curing, the chemically modified fibers are repulped in a Waring Blendor for 1 minute on low speed. The procedure yields fibers having a wet weight of 186.77 g and consistency of 2.57%, from which the Fiber Yield is calculated to be 4.80 g. The Conversion is about 95%. The WAARV is determined to be 35.9 g/g.

EXAMPLE XXX

Preparation of wet-laid paper comprising fiber of the invention (Example VII) in admixture with conventional fiber A slurry of northern softwood Kraft pulp (NSK) is prepared by repulping NSK dry-lap (1.75 g bone-dry basis) in 400 ml of distilled water in a Waring Blendor on low speed for 1.0 minute. The slurry is placed in a 1 liter beaker and to it is added fiber of the invention (sodium form, made according to Example VII but never dried, 0.75 g bone-dry basis, in 100 ml of distilled water). The pH of the slurry is adjusted to 8.5 with 0.1 Molar sodium hydroxide and the slurry is stirred for 1 hour. A deckle box is fitted with a forming wire (Albany International-Appelton Wire Division, Appelton, Wis.; Handsheet style/mesh 78-S) and is filled with distilled water which is also adjusted to pH 8.5 with 1 Molar sodium hydroxide. The slurry is added and the water is drained by suction. The wet paper sheet (handsheet) thus formed is transferred to a drying fabric (albany International-Appelton Wire Division, Appelton, Wis.; Handsheet style/mesh 36-C) by passage over a vacuum slit on low setting. The drying fabric is passed over the vacuum slit two additional times on high setting and then another fabric is placed on top of the wet handsheet. The sandwhich is passed through a drum dryer at 230° F. until the sheet is dry. This gives a 2.50 g handsheet (basis weight=16.5 lbs/3,000 square feet) containing 30% by weight of fiber of the invention. This handsheet is quick-wicking and has a WAARV of 22.6 g/g. The handsheet can be wetted and re-dried: on rewet, it is found to have preserved good absorbency and wicking characteristics.

EXAMPLE XXXI

Preparation of wet-laid paper comprising fiber of the invention (Example VIII) in admixture with conventional fiber.

The procedure of Example XXX is repeated except that the fiber of the invention of Example VIII is used. The WAARV of the handsheet is determined to be 10.7 g/g.

EXAMPLE XXXII

Preparation of wet-laid paper comprising fiber of the invention (Example IX) in admixture with conventional fiber The procedure of Example XXX is repeated except that the fiber of the invention of Example IX is used. The WAARV of the handsheet is determined to be 24.7 g/g.

EXAMPLE XXXIII

Preparation of wet-laid paper comprising fiber of the invention (Example X) in admixture with conventional fiber The procedure of Example XXX is repeated except that the fiber of the invention of Example X is used. The WAARV of the handsheet is determined to be 23.7 g/g.

EXAMPLE XXXIV

Preparation of wet-laid paper comprising fiber of the invention (Example XI) in admixture with conventional fiber The procedure of Example XXX is repeated except that the fiber of the invention of Example XI is used. The WAARV of the handsheet is determined to be 20.7 g/g.

EXAMPLE XXXV

Preparation of wet-laid paper comprising fiber of the invention (Example XII) in admixture with conventional fiber The procedure of Example XXX is repeated except that the fiber of the invention of Example XII is used. The WAARV of the handsheet is determined to be 19.8 g/g.

EXAMPLE XXXVI

Preparation of wet-laid paper comprising fiber of the invention (Example XIII) in admixture with conventional fiber The procedure of Example XXX is repeated except that the fiber of the invention of Example XIII is used. The WAARV of the handsheet is determined to be 18.7 g/g.

EXAMPLE XXXVII

Preparation of wet-laid paper comprising fiber of the invention (Example XIV) in admixture with conventional fiber The procedure of Example XXX is repeated except that the fiber of the invention of Example XIV is used. The WAARV of the handsheet is determined to be 15.5 g/g.

EXAMPLE XXXVIII

Preparation of wet-laid paper comprising fiber of the invention (Example XV) in admixture with conventional fiber The procedure of Example XXX is repeated except that the fiber of the invention of Example XV is used. The WAARV of the handsheet is determined to be 29.2 g/g.

EXAMPLE XXXIX

Preparation of wet-laid paper comprising fiber of the invention (Example XVI) in admixture with conventional fiber The procedure of Example XXX is repeated except that the fiber of the invention of Example XVI is used. The WAARV of the handsheet is determined to be 19.8 g/g.

EXAMPLE XL

Preparation of wet-laid paper comprising fiber of the invention (Example XVII) in admixture with conventional fiber The procedure of Example XXX is repeated except that the fiber of the invention of Example XVIII is used. The WAARV of the handsheet is determined to be 18.6 g/g.

EXAMPLE XLI

Preparation of wet-laid paper comprising fiber of the invention (Example XVIII) in admixture with conventional fiber The procedure of Example XXX is repeated except that the fiber of the invention of Example XVIII is used. The WAARV of the handsheet is determined to be 9.6 g/g.

EXAMPLE XLII

Preparation of wet-laid paper comprising fiber of the invention (Example XIX) in admixture with conventional fiber The procedure of Example XXX is repeated except that the fiber of the invention of Example XIX is used. The WAARV of the handsheet is determined to be 7.0 g/g.

EXAMPLE XLIII

Preparation of wet-laid paper comprising fiber of the invention (Example XX) in admixture with conventional fiber The procedure of Example XXX is repeated except that the fiber of the invention of Example XX is used.

The WAARV of the handsheet is determined to be 5.7 g/g.

EXAMPLE XLIV-LII

Preparation of wet-laid paper comprising fiber of the invention

The procedures of Examples XXX-XLIII are repeated except that 2.00 g of northern softwood Kraft dry-lap (bone-dry basis) and 0.50 g of the fiber of the invention (bone-dry basis) are used. This give 2.50 g handsheets (basis weight = 16.5 lbs./3,000 square feet) containing 20% by weight of the fiber of the invention. The results are as follows.

| Example No. | Handsheet WAARV (g/g) |
| --- | --- |
| XLIV | 15.6 |
| XLV | 8.5 |
| XLVI | 13.2 |
| XLVII | 14.0 |
| XLVIII | 10.0 |
| XLIX | 12.8 |
| L | 11.6 |
| LI | 11.8 |
| LII | 19.0 |
| LIII | 13.1 |
| LIV | 13.4 |
| LV | 6.4 |
| LVI | 6.8 |
| LVII | 5.6 |

TEST METHODS

Weight average molecular weight of poly(acrylate-co-itaconate)

Weight average molecular weights, $M_W$, of copolymer samples are determined by low angle laser light scattering using a KMX-6 Chromatix Polymer Analyzer (flow injection method). The change in refractive index with concentration, $d_n/d_c$, is measured on a KMX-16 Laser Differential Refractometer at 25° C. after the copolymer solutions are dialyzed against 0.2 Molar sodium chloride in water. The intercept of a linear regression analysis of a plot of $K_C/R_{theta}$ versus c is given by $1/M_W$, where $K = a(n)^2(d_n/d_c)^2$ (the constant a being characteristic of the particular instrument), c = concentration of copolymer, and $R_{theta}$ is the Rayleigh scattering for a given copolymer solution. Typically, the concentrations of copolymer used for molecular weight determinations are 1.0, 1.5, 2.0, 2.5, and 3.0 mg/ml.

pH of aqueous medium; pH in general

In general, pH herein is determined using a conventional digital pH meter which has an accuracy of ±0.01 pH units (Markson model 88). The meter is equipped with a flat surface electrode, which has a peripheral porous polyethylene junction (Markson 12008B). The electrode is particularly suited for measuring the pH of slurries, viscous solutions and wet surfaces. As an alternative, a conventional polymer-gel-filled pH electrode may be used. pH measurements are made at ambient temperature, in the range 20° C.-25° C. The electrodes are calibrated in the conventional manner, using pH 7.00 and pH 4.00 buffers.

It is specifically noted that the above-identified equipment and procedure is used for measuring pH of the aqueous medium discussed hereinabove in the specification.

Consistency

Consistency, such as of wet fiber of the invention, is defined as percentage by weight of a specified fiber, in a slurry, fiber dispersion or wet fiber mass. Measurement is carried out by placing a sample of wet material sufficient to give at least about 0.1 gram of bone dry fiber on a Mettler PM460 balance which is equipped for moisture determination (infra-red dryer model LP16), weighing wet followed by continuous monitoring of weight during drying (90° C. temperature setting) to constant weight.

Fiber Yield

Fiber Yield is defined as the weight in grams, dry basis, of fiber of the invention, sodium form. It is conveniently measured by multiplying the weight of wet, swollen fibers of the invention by the consistency.

Conversion

Conversion is defined as the yield of fiber of the invention expressed in percentage terms. It is calculated by dividing the Fiber Yield by the sum of weights of starting-materials, more specifically the sum of weights, bone dry basis, of poly(acrylate-co-itaconate) plus polyol plus cellulosic fiber starting-material.

In determining Conversion, the weight of poly(acrylate-co-itaconate) in the above is expressed on an acid equivalent basis. That is to say, regardless of the form of the poly(acrylate-co-itaconate) used in the synthesis of the fiber of the invention, and equally regardless of the form of the product fiber, the convention is adopted of everywhere specifying the poly(acrylate-co-itaconate) weight as though it were in the acid form, i.e., all the charge-balancing cations are H. In this manner, the relative proportion of poly(acrylate-co-itaconate) to the cellulose and polyol components is unambiguously determined.

As noted hereinabove, Conversion can be slightly in excess of 100% (typically up to about 106%) as a consequence of cation weight gain. Thus when the poly(acrylate-co-itaconate) starting-material is in the acid form and the fiber of the invention is secured in the sodium form, the heavier sodium cation as compared with hydrogen cations accounts for the additional weight gain.

Water absorbency and retention value (WAARV) of fiber of the invention and WAARV of wet-laid paper containing same The following is a gravimetric water-absorbency and retention-measuring method applicable to characterizing the fibers, pulps or paper webs according to the invention. For purposes of comparison, typical papermaking pulp such as Kraft pulp measures of the order of about 3-4 grams of water per gram of fiber at pH 8.5 ("g/g") by this method and paper webs made from such pulp have similar or slightly lower values. Equipment is as follows:

Sample holders: glass cylinders open at both ends, 1.8 cm. inside diameter, 4.2 cm height.

Tea-bag material: Tea-bag paper, grade 1234T, obtainable from C. H. Dexter Division of the Dexter Corp., Windsor Locks, Conn. This paper is cut into 4.7×9.5 cm rectangles. The purpose of the tea-bag material is to provide a substantially non-absorbent pulp-retaining material through which water will pass during centrifugation, and which acts to prevent the possibility of obtaining artificially high pulp absorbencies, which might otherwise occur, e.g., if the pulp were allowed to block the constriction in the centrifuge tube.

Balance: 0.0001 g sensitivity.

Centrifuge: clinical model, variable speed, with a swinging bucket rotor, four 29.4 mm. inside diameter×95 mm depth shields, and tachometer adapted to measure centrifuge speed.

Centrifuge tubes: designed with a constriction so that on centrifuging, the water will separate into the lower half of the tube, leaving the sample and "tea-bag" in the upper half.

Drying beakers: 10 ml capacity.

Vacuum oven: capable of approximately 250 mTorr vacuum, heating to at least 110° C.; temperature thermostatted at 60° C.

Convection oven: thermostatted at 105° C.

Soaking beakers: 150 ml capacity.

For each absorbency determination, a number of replicated measurements (typically two will suffice provided that the results are in good agreement) are made, each based on the following procedure:

Weigh a tea-bag paper. The weight is the Initial Teabag Weight (Initial Teabag Weight=ITB) and is typically of the order of 70 mg.

Place the fiber or paper (shredded in small pieces) which is to be tested for absorbency into a 150 ml beaker. Add 100 ml distilled water. Adjust pH to 8.5 with aqueous sodium hydroxide. Equilibrate by allowing to stand for about 2 hours.

Fold a weighed tea-bag paper to make a cylindrically shaped holder having one end closed and the other end open. Place it inside a glass cylinder. Into the shaped tea-bag, place wet equilibrated material to be tested, allowing excess water to drain through the tea-bag, until the tea-bag is substantially full with wet fiber. (Typically when the sample to be tested in fiber of the invention, the sample size is sufficient to contain about 100 mg bone dry fiber; when the sample to be tested is a wet-laid paper containing the fiber of the invention, the sample size is sufficient to contain about 300 mg in total of all fiber present; and when the sample to be tested is conventional fiber, e.g., northern softwood Kraft, the sample size is sufficient to contain about 500 mg of fiber. Slip the tea-bag out of the glass cylinder or holder and, preserving the cylindrical shape of the tea-bag, place it and its sample contents in a centrifuge tube. Centrifuge at approximately 125 "g" (gravities) force for 10 minutes, centifuge speed-up time not included. Place the centrifuged sample and tea-bag in an accurately preweighed dry beaker (dry beaker weight=DBW). Weigh the centrifuged sample, tea-bag and beaker (weight=$W_1$). Dry in the 105° C. convection oven for 3 hours. Further dry in the vacuum oven for 6 hours or more. Allow to cool in a desiccator. Weigh (weight=$W_2$). The water absorbency and retention value (WAARV) of the sample (g/g) is given by the following formula:

$$WAARV = (WPW - DPW)/DPW$$

wherein WPW = wet pulp weight = $W_1 - (ITB + DBW)$ and DPW = dry pulp weight = $W_2 - (ITB + DBW)$. In principle, it is possible to measure WAARV absorbency at pH values other than 8.5 of the above-specified method. However, unless there is a specific mention of another pH, any WAARV absorbency value quoted throughout the instant specification and claims, expressed simply in g/g, is strictly to be construed as a measurement at a pH of 8.5.

What is claimed is:

1. A chemically modified fiber having a water absorbency and retention value in the range from about 15 g/g to about 130 g/g comprising, chemically bonded together:
   (a) a cellulosic fiber selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood sulfite pulp fiber, unbleached softwood sulfite pulp fiber, cotton linters, mercerized dissolving pulp fiber, unmercerized dissolving pulp fiber, and mixtures thereof;
   (b) a poly(acrylate-co-itaconate) having a weight average molecular weight in the range from about 60,000 to about 1,000,000, an acrylate content of from about 50 mole % to about 99 mole % and an itaconate content of from about 1 mole % to about 50 mole %, and
   (c) a polyol;

wherein the proportion by weight of said poly(acrylate-co-itaconate) to polyol is from about 250:1 to about 3:1 and the weight of said poly(acrylate-co-itaconate) plus said polyol per unit weight of said cellulosic fiber, (a), is in the range from about 0.3 to about 2, the poly(acrylate-co-itaconate) weight being expressed on an acid equivalent basis.

2. A chemically modified fiber according to claim 1 wherein said cellulosic fiber, (a), is selected from the group consisting of chemithermomechanical pulp fiber, bleached hardwood Kraft pulp fiber, bleached softwood Kraft pulp fiber, unbleached hardwood Kraft pulp fiber, unbleached softwood Kraft pulp fiber, bleached softwood sulfite pulp fiber, unbleached softwood sulfite pulp fiber, and mixtures thereof; said poly(acrylate-co-itaconate) has weight average molecular weight in the range from about 400,000 to about 1,000,000; said acrylate content is from about 70 mole % to about 98 mole %; said itaconate content is from about 2 mole % to about 30 mole %; and said polyol is selected from the group consisting of polethylene glycol, polyvinyl alcohol, ethylene glycol, propylene glycol, glycerin and pentaerythritol.

3. A chemically modified fiber according to claim 2 wherein said polyol has formula $HO(CH_2CH_2O)_nH$ wherein n is from about 4 to about 154 and said proportion by weight of poly(acrylate-co-itaconate) to polyol is from about 30:1 to about 4:1.

4. A chemically modified fiber according to claim 3 wherein said poly(acrylate-co-itaconate) has acrylate content of from about 90 mole % to about 95 mole % and itaconate content of from about 5 mole % to about 10 mole %; said weight average molecular weight is in the range from about 600,000 to about 900,000; n in said formula is from about 34 to about 100; and said weight of poly(-acrylate-co-itaconate) plus polyol per unit weight of said cellulosic fiber, (a), is in the range from about 0.6 to about 1.5.

5. A chemically modified fiber according to claim 4 wherein said water absorbency and retention value is in the range from about 30 g/g to about 100 g/g.

6. A chemically modified fiber according to claim 5 wherein n is said formula is from about 70 to about 80; said proportion by weight of poly(acrylate-co-itaconate) to polyol is from about 10:1 to about 5:1; and said weight of poly(acrylate-co-itaconate) plus polyol per unit weight of cellulosic fiber, (a), is in the range from about 0.8 to about 1.2.

7. A chemically modified fiber according to claim 6 wherein said water absorbency and retention value is in the range from about 50 g/g to about 90 g/g.

8. A chemically modified fiber according to claim 7 wherein the cations, which are inherently present in a charge-balancing amount, are selected from the group consisting of sodium, potassium, lithium, hydrogen and mixtures thereof.

9. A chemically modified fiber according to claim 8 wherein said cations are selected from the group consisting of sodium, hydrogen and mixtures thereof.

10. A cellulosic papermaking pulp consisting essentially of the chemically modified fiber of claim 1.

11. A cellulosic papermaking pulp consisting essentially of the chemically modified fiber of claim 9.

12. A cellulosic papermaking pulp according to claim 11 wherein the content of cations which are hydrogen is such as to produce a pH of less than 5 when dispersed in water.

13. A cellulosic papermaking pulp according to claim 11 wherein the content of cations which are hydrogen is such as to produce a pH of about 6 to about 9 when dispersed in water.

14. A cellulosic papermaking pulp consisting essentially of:
from about 5% to about 60% of the chemically modified fibers of claim 11 and from about 40% to about 95% of conventional cellulosic fiber.

* * * * *